United States Patent [19]
Lemelson

[11] Patent Number: 5,948,272
[45] Date of Patent: Sep. 7, 1999

[54] SYSTEM AND METHOD FOR DETECTING AND NEUTRALIZING MICROORGANISMS IN A FLUID USING A LASER

[76] Inventor: Jerome H. Lemelson, 930 Tahoe Blvd. Suite 286 Unit 802, Incline Village, Nev. 89451-9436

[21] Appl. No.: 08/571,273

[22] Filed: Dec. 12, 1995

Related U.S. Application Data

[63] Continuation-in-part of application No. 08/173,972, Dec. 28, 1993, Pat. No. 5,480,562, and application No. 08/401,193, Sep. 19, 1994, which is a continuation of application No. 07/873,421, Apr. 13, 1992, abandoned, which is a continuation-in-part of application No. 07/309,701, Feb. 10, 1989, abandoned, which is a continuation-in-part of application No. 06/857,055, Apr. 29, 1986, Pat. No. 4,803,992.

[51] Int. Cl.$^6$ .............................. B01D 17/12; A61B 6/00; G01N 21/00; G01N 35/00
[52] U.S. Cl. ......................... 210/745; 210/96.1; 356/318; 422/82.05; 436/55; 436/164; 600/407; 604/19; 604/50
[58] Field of Search .............................. 210/85, 94, 96.1, 210/143, 198.1, 745, 746, 748, 764, 614; 422/62, 82.05, 82.08, 82.09; 436/39, 55, 164, 172; 364/497, 500, 525; 356/318, 411, 436, 39, 301; 348/552; 128/633, 637, 653.1

[56] References Cited

U.S. PATENT DOCUMENTS

| | | |
|---|---|---|
| 4,671,256 | 6/1987 | Lemelson . |
| 4,802,761 | 2/1989 | Bowen et al. ........................... 356/301 |
| 4,803,992 | 2/1989 | Lemelson ................................ 128/634 |
| 4,832,483 | 5/1989 | Verma ..................................... 356/301 |
| 4,889,129 | 12/1989 | Dougherty et al. . |
| 5,017,007 | 5/1991 | Milne et al. ............................ 356/301 |
| 5,242,602 | 9/1993 | Richardson et al. .................... 210/745 |
| 5,351,686 | 10/1994 | Stever et al. ............................ 128/633 |
| 5,380,440 | 1/1995 | Chipps .................................... 210/745 |
| 5,464,013 | 11/1995 | Lemelson ................................ 606/11 |
| 5,480,562 | 1/1996 | Lemelson ................................ 210/94 |
| 5,506,096 | 4/1996 | Helmo ..................................... 210/614 |
| 5,525,240 | 6/1996 | Lemelson ................................ 210/745 |
| 5,543,329 | 8/1996 | Bedell ..................................... 436/164 |
| 5,634,922 | 6/1997 | Hirano et al. ............................ 606/12 |

OTHER PUBLICATIONS

"Enhancement of Luminescence and Raman Spectroscopy by Phase–Resolved Background Suppression", pp. 538–545, Anal. Chem. 1985, vol. 57, Demas et al.

"Use of water Raman Emission to Correct Airborne Laser Fluorosensor Data for Effects of Water Optical Attenuation", pp. 2889–2905, Applied Optics, Sep. 1981, vol. 20, No. 17. Bristow et al.

"Matrix Isolation Raman Spectroscopy", pp. 97–98, Optics and Laser Technology, Apr. 1980, King et al.

"Microprocessor–Controlled Data Acquisition System for Pulsed Laser SpectROscopy" Ritz et al, Applied Spectroscopy, vol. 32, No. 5, (Sep.–Oct. 1978).

"Digital Control of a Raman Spectrometer by a Small Computer and its Application to Soft Mode Spectroscopy", Japanese Journal of Applied Physics, vol. 17, No. 9, pp. 1643–1650 (Sep. 1978).

"Remote Determination of the Concentration of Impurities in Water by the Laser Spectroscopy Method with Calibration by Raman Scattering", Klyshko et al Soviet Physics Dokl. 23(1) Jan. 1978.

*Primary Examiner*—Joseph W. Drodge
*Attorney, Agent, or Firm*—Niro, Scavone, Haller & Niro

[57] ABSTRACT

A system and method is disclosed for detecting and neutralizing disease producing organisms in a body fluid of a patient or in any fluid used for biological experimentation, testing, or production. The system may comprise a laser for irradiating the organisms and a photodetector for detecting radiation emanating from the organisms and an additional optical scanning device which may be a video camera. A computer analyzes scanning signals generated by the scanning device and controls a means for neutralizing the organisms, such as a chemical injector or radiation source, in accordance with the scanning signals. The system may also be used to purify water for drinking or bathing purposes by employing an optical scanning device for detecting organisms in the water such as bacteria, algae, or viruses.

14 Claims, 3 Drawing Sheets

SYSTEM AND METHOD FOR DETECTING AND NEUTRALIZING MICROORGANISMS IN A FLUID USING A LASER

RELATED APPLICATIONS

This is a continuation-in-part of application Ser. No. 08/173,972 filed on Dec. 28, 1993, now U.S. Pat. No. 5,480,562, and a continuation-in-part of presently pending application Ser. No. 08/401,193 filed Sep. 19, 1994 which is a continuation of Ser. No. 07/873,421 filed Apr. 13, 1992, now abandoned, which is a continuation-in-part of Ser. No. 07/309,701 filed Feb. 10, 1989, now abandoned which is a continuation-in-part of Ser. No. 06/852,057 filed Apr. 29, 1986, now U.S. Pat. No. 4,803,992.

BACKGROUND AND SUMMARY OF THE INVENTION

This invention relates to a system and method for detecting and neutralizing microorganisms or toxic substances in a fluid. The fluid may be a body fluid such as blood. The system may also be employed for purifying other fluids such as drinking water and pool water. The fluid is purified or neutralized by controllably killing or otherwise neutralizing bacteria, viruses, as well as other microorganisms or organic matter therein under the control of a computer. In a preferred embodiment, all or a sample of the fluid to be purified is scanned with an electro-optical scanning device, such as a laser and one or more photoelectric detectors of reflected or fluorescent radiation from organic matter in the water and/or a television camera for imaging particulates in the water. The resulting image and/or radiation signals are computer processed and analyzed to detect the presence of substrates, such as bacteria or toxic chemicals, and to quantify same over a period of time. The information defining codes generated as a result of such computer analysis are directly or indirectly employed to effect automatic control of one or more devices for neutralizing the fluid as it flows through a conduit and/or while it is held in a container. The fluid neutralization device may comprise a computer controlled injector pump operable to effect the flow of a select quantity of one or more chemicals into the fluid and/or a radiation source such as a generator of microwaves, UV light, laser radiation, or other radiation. Such chemical or radiation is operable to kill or otherwise render harmless organisms or other matter present in the water. As a result of such controlled water purifying action, the operation is optimized with a savings in energy and/or the amount of chemicals used to purify the water. Furthermore, when a chemical agent is employed to kill bacteria, its amount is minimized to reduce the taste of such chemical as well as any other negative effects on persons drinking or bathing in such purified water.

It is a primary object of the invention to detect substrates such as bacteria, viruses, or other organic matter in a fluid.

It is a further object of the invention to quantify substrates such as bacteria, viruses, or other organic matter in a fluid.

It is a further object of the invention to employ electro-optical scanning and purifying devices under control of a computer in order to purify water for drinking or bathing.

It is a further object of the invention to continuously detect and quantify substrates such as bacteria, viruses, or other organic matter in a flowing liquid.

It is a further object of the invention to detect and kill or otherwise neutralize bacteria, viruses, cancerous cell or other organic matter in a body fluid.

Other objects, features, and advantages of the invention will become evident in light of the following detailed description considered in conjunction with the referenced drawings of a preferred exemplary embodiment according to the present invention.

DETAILED DESCRIPTION OF THE INVENTION

Figure 2:
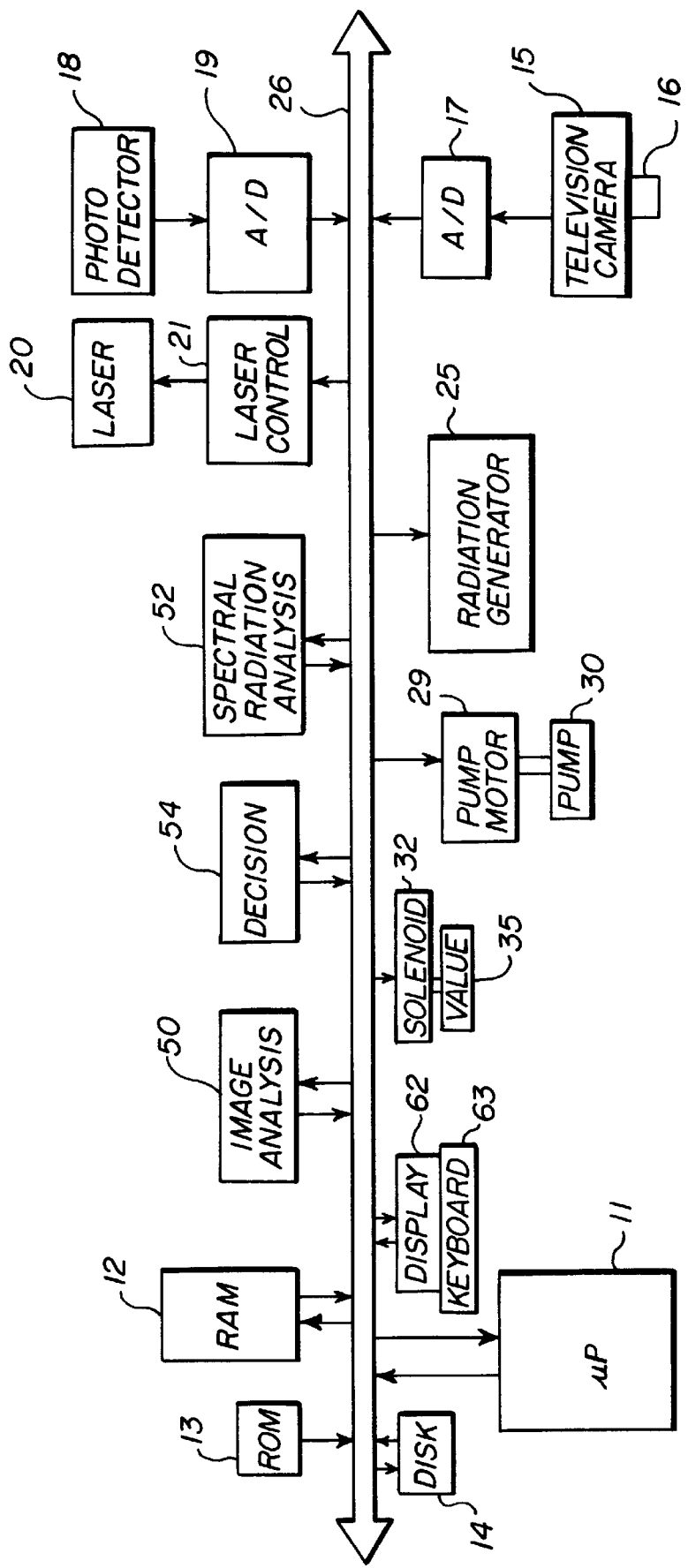
FIG. 2 shows a system for analysis of data generated by electro-optical scanning devices and operation of control elements to purify a fluid.

In FIG. 2 is shown a system 10 for detecting disease causing elements in a liquid such as water or body fluid such as blood, quantizing same and automatically computer controlling one or more means or subsystems for killing or deactivating the disease causing or defining elements in the liquid. The system 10 may be utilized to purify drinking or pool water and/or in a modified form, blood in vitro and/or in vivo by killing harmful or disease defining bacteria, virus, cancer cells and the like therein.

Figure 1A:
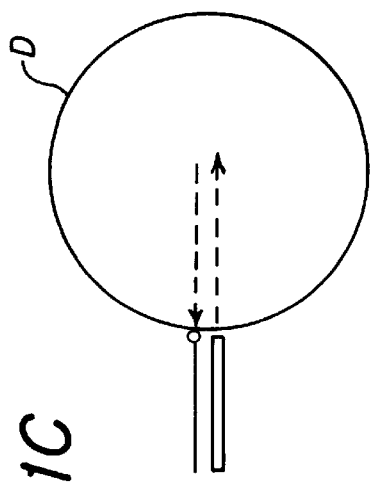
FIGS. 1A through 1D show alternative configurations of a laser and photodetector for detecting microorganisms and other matter within a duct.
Figure 1C:
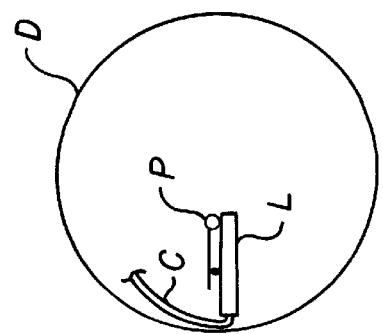
Figure 1B:
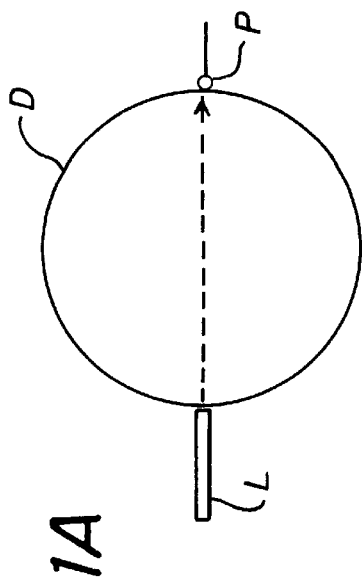
Figure 1D:
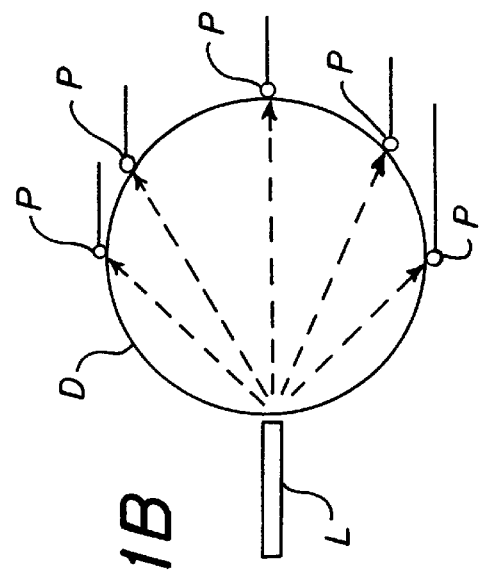

FIGS. 1A through 1D show different alternative arrangements of a laser L and a photodetector P for detecting substrates in a liquid contained within a duct D. The laser L generates a laser beam of fixed frequency or a varying computer controlled group of frequencies or wavelengths which beam (or a plurality of beams from a plurality of lasers L) is passed laterally or oblique to the longitudinal axis of a tube or duct D through which the liquid is flowing. The light beam may also be deflected to scan a plurality of paths in a select (lateral and/or oblique) plane or plurality of planes through the liquid. A transparent window in the duct D, transparent wall of the duct, or the like may pass the laser beam(s) to the liquid and also pass reflections thereof and/or fluorescence or spectral radiation from solids in the liquid back to the photodetector P. The laser and photodetector may be held stationary or may move together in a scanning movement. Alternatively, the laser L and photodetector P may be disposed within the liquid by being mounted in the wall of duct D. The photodetector P may be located relative to the laser L so as to detect scattered or backscattered radiation as shown in FIGS. 1A and 1C, respectively. FIG. 1B shows a plurality of photodetectors arranged so as to detect scattered radiation from laser L or emitted radiation from excited substrates within the duct D. The laser or a light pipe directing such laser radiation L and the photodetector P may also be disposed in the opening of a narrow hypodermic needle or at the end of a catheter C disposed in the tube D, blood vessel, or other body duct as shown in FIG. 1D.

A microprocessor or computer 11 controls the detection and treatment actions by receiving and gating digital detection and control signals to and from various electrically operated devices and subsystems. The microprocessor 11 is shown as connected via a bidirectional data bus 26 to various peripheral components including a RAM 12, a ROM 13, a disk storage device 14, a keyboard 63, a display 62, as well as other components as described below. Scanning of a fluid to detect select elements, such as disease indicating or defining bacteria, viruses, fungae, or other types of select substrates is effected by one or more imaging devices and/or spectral radiation detection devices such as photoelectric detector 18 which may be used alone or with a plurality thereof and one or more attendant lasers 20 to scan across a duct such as a pipe through which water or other liquid is flowing or for scanning blood in a blood vessel. The output of detector 18 is a variable electrical signal which is digitized by an analog to digital converter 19 and passed to data bus 26 for analysis by a spectral radiation analysis module 52. The lasers 20 may be tunable so that the wavelengths of their emitted radiation may be program varied under control of computer 11. Such computer control of the laser tuning may be in accordance with a standard protocol or may be varied in accordance with analysis of previously generated and analyzed scanning signals so as to permit the automatic detection of a variety of different substances or entities in fluid scanned.

In a preferred embodiment, the computed digital code signals output by either or both an image analyzing and spectral radiation signal analyzing modules or computers 50 and 52 are applied by microprocessor 11 to a decision module or computer 54 for analysis using expert systems, fuzzy logic and/or neural network techniques, where the aforementioned modules may be either dedicated hardware components or software programs. The output of decision module 54 generates coded command signals for controlling the operation of one or more pump motors 29 operating pumps 30 and/or solenoids 32 operating valves 35 to flow controlled amounts of chemical and/or biological agents to the water or body fluid to kill or otherwise neutralize or affect the detected disease elements therein.

Such computer generated control signals may be applied to control the operation of one or more radiation generators 25 for generating and applying disease organism killing or neutralizing radiation to a select location or locations of the liquid. The duration and intensity of the applied radiation may be computer controlled in accordance with the type(s) and density of the detected disease elements in the liquid.

Also shown in FIG. 2 is a scanning television camera 15 coupled to scan images of an optical or electron microscope 16 scanning either the liquid in the duct or blood vessel D and/or sample(s) of such liquid automatically removed therefrom as a flow, as individual drops, pools thereof or thin films or smears applied by a robot applicator penetrating the flowing liquid. The image signal output of the TV camera 15 is digitized in an A/D converter 17 and passed to bus 26 for analysis by image analyzing module 50. The TV camera 15 may be employed alone or to provide image signals together with spectral or fluorescence signals obtained by one or more photoelectric detectors sensing spectral radiation from disease elements (cancer cells, bacteria, protozoa, viruses, etc.) in the fluid as they are intersected by exciting laser radiation applied as described.

The system described above may be used for purifying water or other fluid by scanning samples of the water and operating purification equipment such as chemical injectors or radiation sources in accordance with the results of the scanning. The system may also be used to scan a body fluid of a patient (eg., blood or lymph) in order to detect organisms such as bacteria, viruses, or cancer cells and neutralizing the organisms so detected with radiation and/or a chemical or biological agent. The scanning device may be disposed within a blood vessel of the patient by means of a catheter or hypodermic needle or samples of the patient's body fluid may be scanned and neutralized extracorporeally. With proper miniaturization of the electronics and mechanical components, the system 10 may be carried by a person or disposed within a body implant housing to continuously scan body fluids for cancer cells or foreign organisms, detect same, and apply laser radiation or inject a drug or other chemical agent to kill or otherwise treat same. The chemical agent may be injected directly from the implant or from a separate injection needle inserted into an artery or vein under control of the onboard computer. Similarly, laser radiation may be transmitted via a light pipe inserted into the body or produced by a laser within the implant.

Figure 3:
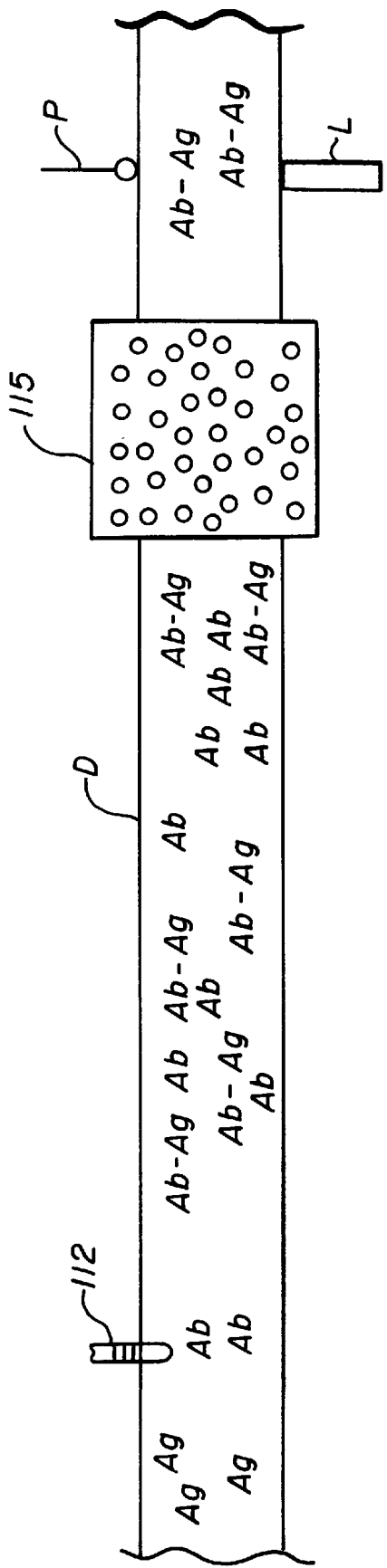
FIG. 3 shows a system for quantizing the amount of substrate in a flowing liquid.

FIG. 3 shows an embodiment of the present invention where the fluid to be analyzed is passed through a conduit or duct D which may be either a section of a primary conduit transporting the fluid or a sidestream sample from a conduit or other fluid containing structure. A predetermined quantity of a fluorescent-labeled substance having a specific binding affinity for a selected substrate (such as a bacterium, viral particle, or molecule) whose presence is to be detected or quantified is then injected into the sample stream from injection nozzle 112. The labeled binding substance may typically be antibodies Ab, either in the form monoclonal antibodies or labeled antiserum containing such antibodies, which react with antigenic determinants Ag on the substrate. After mixing with the sample fluid, the antibodies form Ab-Ag complexes with any substrate present in the fluid. An excess of antibodies is used to ensure that all the substrate present reacts with antibody. Next, the fluid is passed through a reaction vessel 115 in which any unbound antibodies react with immobilized antigen corresponding to antigenic determinants present on the substrate. The reaction vessel 115 may take any number of forms, such as a column of inert material (eg., cellulose or agarose) to which antigen is attached. The amount of immobilized antigen presented to the fluid is such that all unbound antibodies react with the antigen and are thus essentially cleared from the solution. This means that the material within the reaction vessel 115 should be periodically cleaned or changed in order to contain sufficient unreacted immobilized antigen to clear the fluid of unbound antibodies. After passing through reaction vessel 115, the fluid contains labeled Ab-Ag complexes consisting of antibody bound to substrate particles. One type of label which may be conjugated to the antibody is a fluorescent label such as fluorescein or rhodamine which are commonly used in flow cytometry. The Ab-Ag complexes are detected by means of a laser L for exciting the fluorescent dye molecules and a photodetector P for measuring the light scattered and/or emitted by the fluorescent molecules. The laser is operated in a scanning fashion so that the beam intersects with a large portion of the fluid passing by. The signal produced by the photodetector P varies in accordance with the amount of substrate present in the sample fluid and is fed to the computer 11. The computer is thus able to detect whether or not the substrate is present or, by comparing the photodetector signal to standard values and taling into account the fluid flow rate and number of antigenic sites on the substrate particles, quantify the amount of substrate present. The present invention thus allows the continuous monitoring and/or quantification of substrates in a flowing fluid. As described above, if the substrate is detected within the fluid, the computer 11 may then operate a mechanism such as a chemical injector and/or radiation source to destroy or otherwise neutralize the substrate and thus purify the fluid.

The embodiment described above uses labeled antibodies which bind to antigenic determinants on the substrate particles in order to detect their presence. Certain substrates, however, can react with other types of ligands which may be labeled and detected in a similar manner. For example, labeled protein A from *staphylococcus aureus* or lectins such as conconavilin A may be used to detect the presence of immunoglobulins or carbohydrates, respectively, in the sample fluid. Labeled antibodies may also be used in an indirect method in which antibodies directed against the substrate are reacted with substrate particles as described above and then reacted with labeled anti-Ig antibody to allow the detection and/or quantification of the substrate.

In another embodiment, radiation from laser 20 is employed to cause the fluorescence of certain specific molecules already present in the fluid and which are associated with the target microorganisms or toxic substances. When the target microorganism or toxic substance is associated with such a fluorescent molecule, radiation emitted at the wavelength at which the molecule fluoresces is detected by photodetector 18 and analyzed by computer 11 to indicate the presence of, or quantify the amount of, the target microorganisms or toxic substance in the fluid. By controllably varying the frequency of the light emitted by laser 20 and that detected by photodetector 18, a number of different molecules associated with different target organisms or substances may be scanned for.

Although the invention has been described in conjunction with the foregoing specific embodiments, many alternatives, variations, and modifications will be apparent to those of ordinary skill in the art. Those alternatives, variations, and modifications are intended to fall within the scope of the following appended claims.

What is claimed is:

1. A method for detecting and neutralizing microorganisms in a body fluid from a patient comprising the steps of:

(a) scanning a select amount of said fluid with a laser and generating scanning signals containing information indicative of the presence of select microorganisms in the fluid;

(b) computer processing and analyzing said scanning signals and generating code signals relating thereto; (c) employing said code signals to control the operation of a device, other than said laser, for neutralizing the microorganisms so detected.

2. A method in accordance with claim 1 wherein said neutralizing step is performed by irradiating the organisms with lethal radiation.

3. A method in accordance with claim 1 further comprising the steps of using said scanning signals to quantify the amount of organisms in the body fluid, generating a code signal indicative thereof, and performing said neutralizing step in accordance with said code signal.

4. A method in accordance with claim 1 wherein said scanning step is performed with a laser for irradiating organisms in the body fluid with laser radiation and a photodetector for detecting fluorescence radiation emitted from said organisms.

5. A method in accordance with claim 1 wherein said scanning step is performed with a laser for irradiating organisms in the body fluid with laser radiation and a photodetector for detecting radiation scattered by said organisms.

6. A method in accordance with claim 1 wherein the method is performed extracorporeally on samples of the patient's blood.

7. A method in accordance with claim 1 further comprising the step of controlling the operation of said laser with said code signals generated from said scanning signals.

8. A system for detecting and neutralizing biological organisms in a fluid comprising:

(a) a laser for scanning a fluid and generating scanning signals containing information indicative of the presence of select organisms in the fluid;

(b) a computer for processing and analyzing said scanning signals and generating code signals relating thereto;

(c) a device, other than said laser, under the control of said computer and operated in accordance with said code signals for neutralizing the organisms so detected, (d) means for controllably varying radiation emanating from said laser during scanning to detect different organisms in the fluid.

9. A system in accordance with claim 8 wherein said laser operates to irradiate organisms in the fluid with laser radiation and further comprising a photodetector for detecting radiation emanating from organisms in the fluid.

10. A system in accordance with claim 8 wherein said neutralizing device is an injector for delivering a chemical agent into the fluid.

11. A system in accordance with claim 8 wherein said neutralizing device is a radiation generator for irradiating the organisms with lethal radiation.

12. A system in accordance with claim 8 wherein said radiation detected by said photodetector and employed to generate code signals is laser radiation scattered by organisms in the fluid.

13. A system in accordance with claim 8 wherein said laser is a tunable laser controlled by said computer so that the laser may be controllably varied in frequency during scanning to detect different biological substrates in the fluid.

14. A system in accordance with claim 8 wherein the operation of said laser is controlled in accordance with said code signals generated from said scanning signals.

\* \* \* \* \*